United States Patent [19]

Cortner, Jr. et al.

[11] 4,091,809
[45] May 30, 1978

[54] PARTIALLY TRANSPARENT EYESHIELD

[75] Inventors: William C. Cortner, Jr.; Rogers C. Daniels, both of St. Joseph, Mo.

[73] Assignee: Philips Roxane, Inc., St. Joseph, Mo.

[21] Appl. No.: 733,477

[22] Filed: Oct. 18, 1976

[51] Int. Cl.² .............................................. A61F 13/12
[52] U.S. Cl. ..................................................... 128/163
[58] Field of Search .................. 128/163, 132 R, 155, 128/154; 2/9, 14, 15

[56] References Cited

U.S. PATENT DOCUMENTS

| | | | |
|---|---|---|---|
| 1,642,661 | 9/1927 | Robinson | 128/163 |
| 1,917,117 | 7/1933 | Hines | 128/163 X |
| 2,165,668 | 7/1939 | Vaccaro | 128/163 X |
| 3,092,103 | 6/1963 | Mower | 128/132 R |
| 3,973,561 | 8/1976 | Kane | 128/132 R |

FOREIGN PATENT DOCUMENTS 69,430  1/1915  Austria ................................. 128/163

*Primary Examiner*—John D. Yasko
*Attorney, Agent, or Firm*—K. M. LeFever; Norman N. Spain

[57] ABSTRACT

An eyeshield for protecting an eye of a domestic animal or human from sunlight, insects and dust while permitting vision is formed of an upper light opaque lid covering portion joined to a lower eye protecting portion formed of a light and moisture permeable but insect and dust impermeable portion. A portion of the shield extends outwardly along the line of attachment between the upper and lower portions, thus acting as a sunshade and the novel sunshade is formed so as to have a convex shape outward from the eye when worn.

10 Claims, 7 Drawing Figures

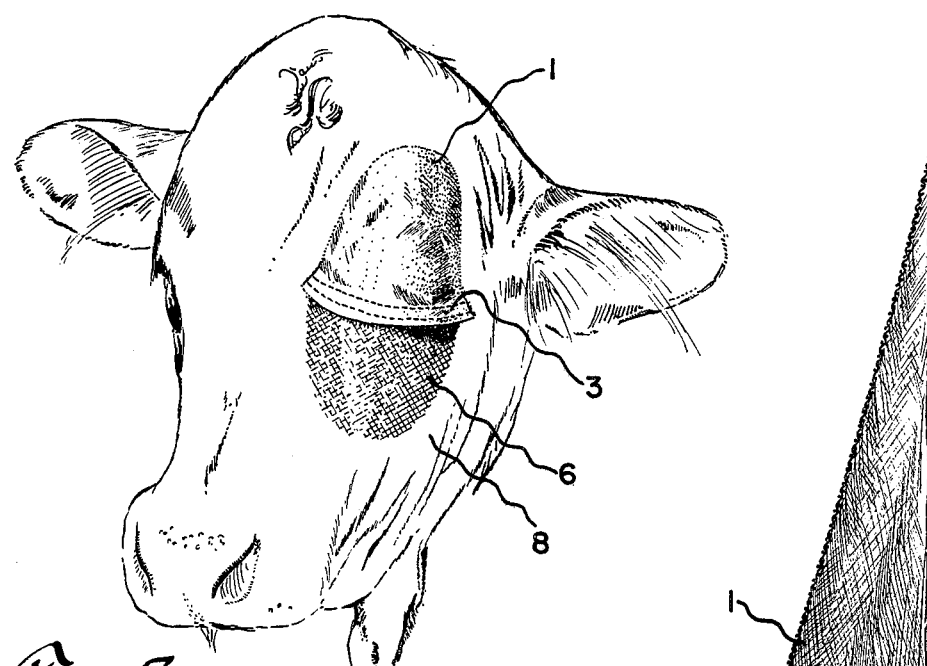
Fig. 5
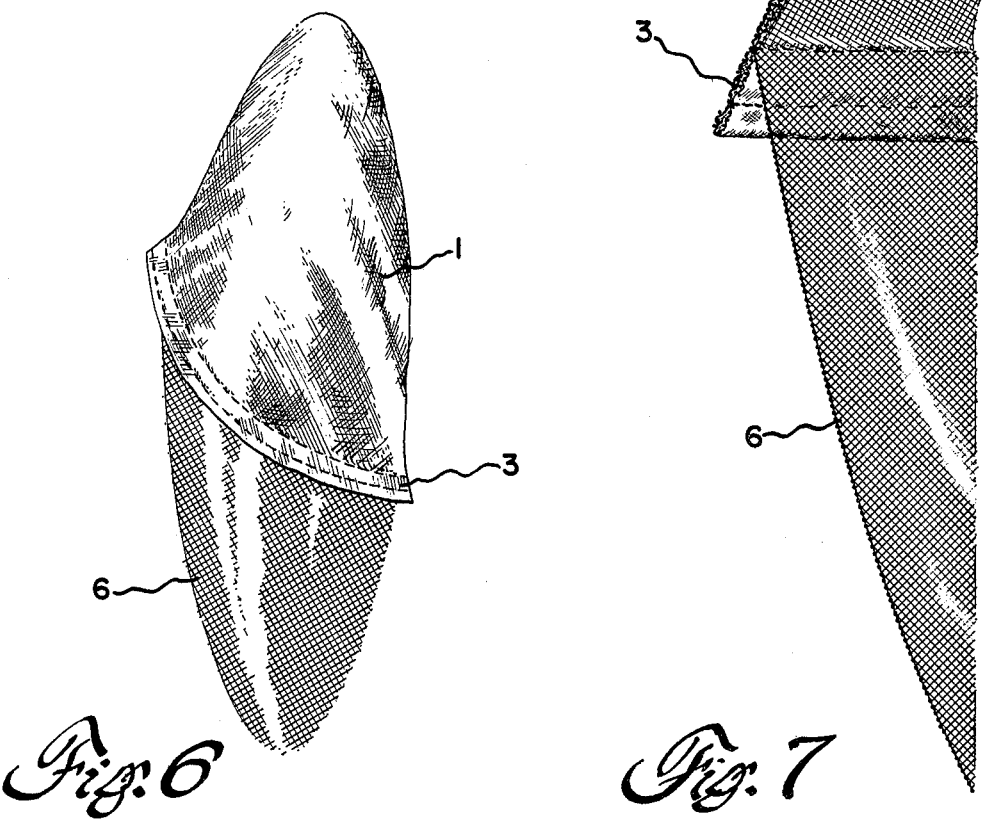
Fig. 6
Fig. 7

PARTIALLY TRANSPARENT EYESHIELD

BACKGROUND OF THE INVENTION

The invention relates to a novel eyeshield for humans and domestic animals that is adhesively or otherwise attached to the face of the wearer.

There are many conditions affecting eyes of humans and domestic animals where it is necessary to protect a diseased or otherwise irritated eye from insects, sunlight and other irritants.

For example, in order to prevent spreading of pinkeye (infectious keratoconjunctivitis) among cattle, it is usually necessary to isolate the infected animal, as the disease is transmitted by means of flies, including the common housefly and stable fly. In addition, it is necessary to protect the infected eye from such irritants as sunlight, dust, pollen and insects in general which tend to seriously aggrevate the condition.

In order to prevent spreading of the disease without need for isolation of the infected animal and in order to prevent irritants from reaching the infected eye, it has been known to adhesively attach an opaque eye patch made of a dark, closely woven cloth material to the face of the animal or an eye patch made of laminated opaque material as described in U.S. Pat. No. 3,973,561.

While such eye patches prevent sunlight, insects, and other irritants from reaching the infected eye, these eye patches have the disadvantages of completely eliminating vision from the infected eye, allowing an undesirable amount of moisture and heat to build up in the vicinity of the eye and to require removal of the eye patch in order to administer medication to the eye.

In other eye diseases suffered by domestic animals such as horses and pigs as well as humans, particularly infants and physically disabled persons, the prior art eye patches also exhibit similar disadvantages.

SUMMARY OF THE INVENTION

The present invention provides a unique eyeshield for domestic animals and humans, which while providing the advantages of the prior art eye patches, is free of the disadvantage of the known eye patches.

Briefly, the eyeshield of the invention is constructed so as to protect the eye from sunlight, insects, pollen and other irritants while not preventing vision and allowing free passage of air and moisture to the eye.

This eyeshield is formed of an upper lid protecting section formed of an opaque closely woven cloth attached to a lower eye protecting section formed of a cloth web pervious to light and moisture but impervious to insects, dust and other eye irritants. The upper and lower portions of the eyeshield are joined in such a manner that a protrusion extends outwardly from the device along the line of attachment between the upper and lower portions and the eyeshield assumes a convex configuration, from a normally essentially flat configuration, when it is the eye surrounding position.

The eyeshield of the invention has the advantages of preventing direct sunlight, insects and other irritants from reaching the eye while providing little or no interference with vision and preventing heat and moisture build-up occurring around the eye. In addition, due to the relatively open weave of the lower or eye covering portion of the instant eyeshield, it is possible to apply medication directly to the eye by spraying, without removal of the shield from the eye.

The eyeshield may be made of any suitable cloth. However, relatively stiff materials are preferred, generally in dark colors.

Thus the upper, lid-covering portion may be made of canvas, such as a heavy duty cotton duck, a closely woven cloth made of a synthetic fibre such as polypropylene, polyester, such as Dacron or nylon.

The lower, or eye-covering portion may be made of any suitable mesh which has little or no tendency to unravel. Some examples of such materials are nylon, Dacron or polypropylene mesh.

The openings in the mesh should be large enough to provide a minimum interference with vision and allowing free passage of air and liquids while at the same time being small enough to keep insects, pollen and other solid irritants from coming in contact with the eye.

A mesh size of 30 to 40 is preferred.

The eyeshield may have any suitable shape, as long as it covers the eye and upper eyelid. In general, both the upper and lower portions, when joined together, form an oblong figure, such as an elipse or a cup-shaped figure.

The eyeshield may be held in place by any suitable means, the particular means depending upon the animal for which it is intended.

For hairy animals such as cattle and sheep, a non-toxic glue such as Pinkeye-Lid Glue, which is first applied to the face of the animal, in the vicinity of the infected eye may be employed.

For humans and animals in which the skin surrounding the eye is free of hair, a contact cement such as employed on Band-Aids or similar type of surgical tape may be employed. In such an event, it is desirable that the eyeshield be supplied with a layer of such a contact cement along a thin inner border surrounding the inner surface of the eyeshield. In such a case, it is preferable that, before use, the border of contact cement be protected with a protective strip of a material having a low degree of adhesion to the contact cement. For example, strips of wax paper or similar low adhering materials may be employed.

In some case, particularly for humans, the eyeshield may be held in place by a strap, band or string or similar means attached to opposing edges of the eyeshield and encircling the head of the animal.

The eyeshield of the invention may be manufactured by any suitable means known in the art.

For example, after being out to a suitable shape, the eye covering portion and the lid covering portion are sewed, stapled or otherwise joined together under compression or tension in such a manner that a wide hem is formed along the line joining the two portions.

However, a particularly advantageous method of manufacturing the eyeshield of the invention and one that is directed to an aspect of the invention is carried out as follows:

Both the opaque lid covering portion and the bottom eye covering mesh portion are cut in the desired form with the tops of both portion being out crosswise with the weave to form a slightly rounded taper of substantially identical configuration. A narrow fold having the width of the desired protrusion is made along the tapered edge of the opaque lid covering portion. At least one vertical slit is cut in the fold. The material in the fold is then so overlapped so as to cover the slit or slits and the top of the fold is then sewed or otherwise fastened down while the fold is in this compressed position. The tapered edge of the eye covering mesh portion is then fitted along the bottom edge of the fold by holding both the upper opaque portion and the lower mesh portion in a position sufficiently compressed to allow the two tapered edges to align with each other and sewing or otherwise joining the two tapered edges together while both portions are in such compressed condition.

BRIEF DESCRIPTION OF THE DRAWING

FIG. 5 is a view of the eyeshield of FIG. 1 as worn by a cow 8.

FIG. 6 is a front view of the eyeshield of FIG. 1 in open or eye-protecting position.

FIG. 7 is a side view of the eyeshield of FIG. 1 when folded along the longitudinal axis joining the web portion 6 to the cloth portion 1.

DETAILED DESCRIPTION OF A PREFERRED EMBODIMENT OF THE INVENTION

Figure 1:
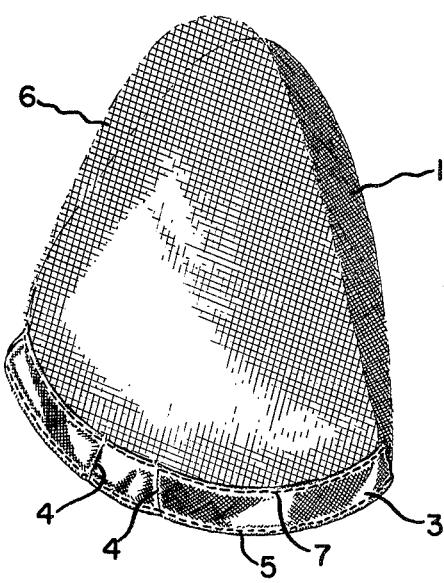
FIG. 1 is a perspective view of the eyeshield of the invention in open or eye-protecting position.
Figure 2:
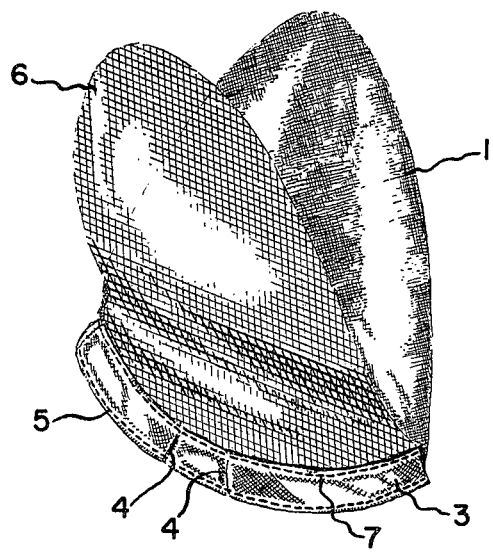
FIG. 2 is another perspective view of the eyeshield of FIG. 1 in open or eye-protecting position.
Figure 3:
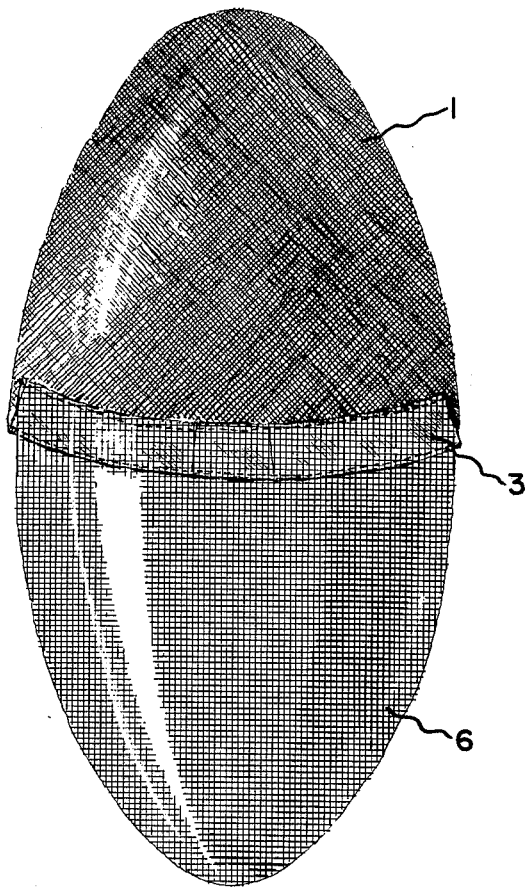
FIG. 3 is a flat view of the eyeshield of FIG. 1.
Figure 4:
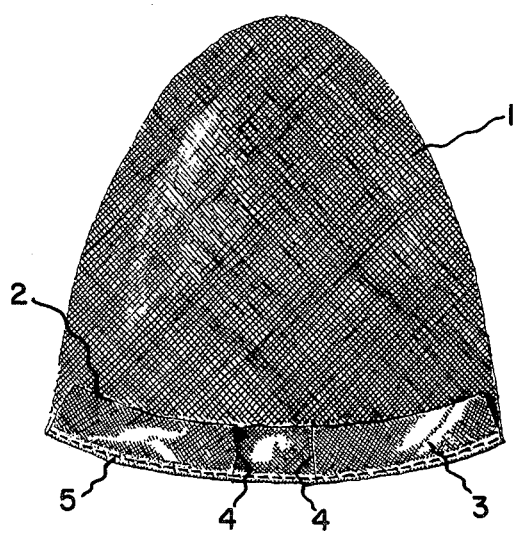
FIG. 4 is a flat view of the upper section during a stage in manufacture of the eyeshield of FIG. 1.

A piece of black heavy cotton duck is cut to form a semi-eliptical shaped piece 1 approximately 4 × 5½ inches. The top portion is cut crosswise with the grain of the cloth to form a tapered edge 2. The tapered edge 2 is then folded to form a narrow fold 3 of about ½ to 1 inch in width approximately parallel to the tapered edge 2. Slits 4 are cut in the fold 3. The material of the fold 3 is then overlapped to cover the slits 3 and a seam 5 is sewn along the top edge of the fold 43 while the material of the fold is in the overlapped or compressed position.

A polypropylene mesh having 30–40 holes per inch is cut also on the taper crosswise with the weave of the cloth to form a piece 6 of approximately the size and shape of the cotton duck piece 1.

The tapered edge of the polypropylene mesh piece 6 is then aligned with the bottom of corresponding tapered edge of the cotton duck piece 1 by holding both pieces in a compressed position and the thus aligned edges of the two pieces are sewed together to form a seam 7.

The eyeshield thus produced may be attached to the eye of a cow for example by applying a coating of a glue such as Pinkeye-Lid Glue to the area surrounding the eye and upper eyelid and the corresponding area of the inner surface of the eyeshield in pressing the eyeshield on with the portion covering the eye and opaque portion covering the upper eyelid.

When worn by the cow, as shown in FIG. 5, the eyeshield assumes a shape convex to the eye and fold 3 forms a projection acting as a sunshield for the eye.

Due to the mesh construction, the animal is able to see through the covered eye and there is no moisture or heat build up in the eyeshield. However, flies, other insects and dust are kept out of contact with the eye. Further, medication is able to be sprayed into the eye through the mesh.

What we claim is:

1. An eyeshield for protecting the eye of a human or domestic animal, said eyeshield comprising an upper eyelid protecting section formed of closely woven cloth, a lower, eye protecting section, pervious to light and moisture but impervious to insects and other solid eye irritants formed of a cloth web and means for attaching said upper section to said lower section along a line of attachment in a manner such that a protrusion extends outwardly from the eyeshield along said line of attachment and the eyeshield assumes a convex configuration, from a normally essentially flat configuration, when in an eye shielding position.

2. The eyeshield of claim 1 wherein the mesh of the eye protecting section has 20–40 holes per inch.

3. The eyeshield of claim 2 wherein the upper eyelid protecting section is made of canvas or duck.

4. The eyeshield of claim 3 wherein the lower eye protecting section is made of polypropylene web, polyester web or nylon web.

5. The eyeshield of claim 2 wherein both the upper and lower section are formed of dark colored cloth.

6. The eyeshield of claim 1 particularly suitable for use by domestic animals adaptable to be adhesively secured to the face of said animal along the border of the inner surface of said eyeshield.

7. The eyeshield of claim 1 wherein the means for attaching is a plurality of stitches.

8. A method of manufacturing the eyeshield useful for humans or animals comprising the steps of cutting out two approximately identically shaped and size pieces of an opaque cloth and a mesh cloth with one common edge cut crosswise with the weave to form a slightly rounded taper, making a narrow fold along the tapered edge of the opaque cloth piece of a width of about that of the desired protrusion, cutting at least one vertical slit in said fold, overlapping the material in said fold to cover the slit or slits, fastening down the top of the fold while in the material is thus overlapped, aligning the corresponding tapered edge of the mesh cloth piece with the bottom edge of the fold in the opaque cloth piece by holding both pieces in a compressed position and then joining the two tapered edges of the two pieces together while both pieces are in said compressed condition.

9. The method of claim 8 wherein the fold is fastened down by sewing.

10. The method of claim 9 wherein the two tapered edges are sewn together.

* * * * *